US 6,727,067 B2

(12) United States Patent
Russman et al.

(10) Patent No.: US 6,727,067 B2
(45) Date of Patent: Apr. 27, 2004

(54) METHODS FOR THE ANALYSIS OF NON-PROTEINACEOUS COMPONENTS USING A PROTEASE FROM A BACILLUS STRAIN

(75) Inventors: Eberhard Russman, Penzberg (DE); Thomas Meier, Munich (DE); Ranier Schmuck, Benediktbeueren (DE); Johnny Staepels, Weilheim (DE); Uwe Wehnes, Ilvesheim (DE)

(73) Assignee: Roche Molecular Systems, Inc., Alameda, CA (US)

( * ) Notice: Subject to any disclaimer, the term of this patent is extended or adjusted under 35 U.S.C. 154(b) by 0 days.

(21) Appl. No.: 10/007,389

(22) Filed: Oct. 29, 2001

(65) Prior Publication Data

US 2003/0165855 A1 Sep. 4, 2003

(51) Int. Cl.[7] .................................................. C12Q 1/68
(52) U.S. Cl. .......................................................... 435/6
(58) Field of Search ........................... 435/287.1, 287.2, 435/288.5, 209, 269, 135, 138, 196, 198, 7.1, 6, 24; 204/545, 547, 403, 409, 643; 514/453; 422/81, 82.01

(56) References Cited

U.S. PATENT DOCUMENTS

| 3,723,250 A | 3/1973 | Aunstrup et al. |
| 4,895,799 A | 1/1990 | Kruse-Muller et al. |
| 6,268,393 B1 * | 7/2001 | Xu et al. .................... 514/453 |

| 2002/0155586 A1 * | 10/2002 | Cheng et al. ............. 435/287.1 |

FOREIGN PATENT DOCUMENTS

| DE | 44 31 432 A1 | 3/1996 | |
| WO | WO 89/06279 | * 7/1989 | ............ C12N/9/50 |
| WO | WO 98/20115 | 5/1998 | |

OTHER PUBLICATIONS

UKNCC Data Sheet, *Bacillus clausii*, NCIMB Accession No. 10309, Strain Type: Bacterium, Strain Name: C360.
UKNCC Data Sheet, *Bacillus circulans*, NCIMB Accession No. 10147, Strain Type: Bacterium, Strain Name C303.
International Search Report for EP 00123728.8–2116, filed Jun. 5, 2001.

* cited by examiner

*Primary Examiner*—Kenneth R. Horlick
(74) *Attorney, Agent, or Firm*—Pennie & Edmonds LLP

(57) ABSTRACT

This invention relates to a method for the analysis of a (at least one) target non-proteinaceous component of a mixture of non-proteinaceous and proteinaceous components derived from a biological sample using a protease from a Bacillus strain. The invention further relates to a method for the analysis of a (at least one) target nucleic acid component of a mixture of non-proteinaceous components, which comprise nucleic acids, and proteinaceous components whereby the mixture is derived from a biological sample comprising the steps of incubating the mixture with a (at least one) protease from a Bacillus strain, optionally amplifying the (at least one) target nucleic acid component, and determining or detecting the (at least one) target nucleic acid component.

33 Claims, 6 Drawing Sheets

SEQUENCE LISTING

<160> NUMBER OF SEQ ID NOS: 12

<210> SEQ ID NO 1
<211> LENGTH: 361
<212> TYPE: PRT
<213> ORGANISM: Bacillus lentus

<400> SEQUENCE: 1

Met Arg Gln Ser Leu Lys Val Met Val Leu Ser Thr Val Ala Leu Leu
 1               5                  10                  15

Phe Met Ala Asn Pro Ala Ala Ala Gly Gly Glu Lys Lys Glu Tyr Leu
            20                  25                  30

Ile Val Val Glu Pro Glu Glu Val Ser Ala Gln Ser Val Glu Glu Ser
        35                  40                  45

```
Tyr Asp Val Asp Val Ile His Glu Phe Glu Ile Pro Val Ile His
        50                  55                  60

Ala Glu Leu Thr Lys Lys Glu Leu Lys Lys Leu Lys Lys Asp Pro Asn
 65                  70                  75                  80

Val Lys Ala Ile Glu Glu Asn Ala Glu Val Thr Ile Ser Gln Thr Val
                 85                  90                  95

Pro Trp Gly Ile Ser Phe Ile Asn Thr Gln Gln Ala His Asn Arg Gly
            100                 105                 110

Ile Phe Gly Asn Gly Ala Arg Val Ala Val Leu Asp Thr Gly Ile Ala
        115                 120                 125

Ser His Pro Asp Leu Arg Ile Ala Gly Gly Ala Ser Phe Ile Ser Ser
    130                 135                 140

Glu Pro Ser Tyr His Asp Asn Asn Gly His Gly Thr His Val Ala Gly
145                 150                 155                 160

Thr Ile Ala Ala Leu Asn Asn Ser Ile Gly Val Leu Gly Val Arg Pro
                165                 170                 175

Ser Ala Asp Leu Tyr Ala Leu Lys Val Leu Asp Arg Asn Gly Ser Gly
            180                 185                 190

Ser Leu Ala Ser Val Ala Gln Gly Ile Glu Trp Ala Ile Asn Asn Asn
        195                 200                 205

Met His Ile Ile Asn Met Ser Leu Gly Ser Thr Ser Gly Ser Ser Thr
    210                 215                 220

Leu Glu Leu Ala Val Asn Arg Ala Asn Asn Ala Gly Ile Leu Leu Val
225                 230                 235                 240

Gly Ala Ala Gly Asn Thr Gly Arg Gln Gly Val Asn Tyr Pro Ala Arg
                245                 250                 255

Tyr Ser Gly Val Met Ala Val Ala Ala Val Asp Gln Asn Gly Gln Arg
            260                 265                 270

Ala Ser Phe Ser Thr Tyr Gly Pro Glu Ile Glu Ile Ser Ala Pro Gly
        275                 280                 285

Val Asn Val Asn Ser Thr Tyr Thr Gly Asn Arg Tyr Val Ser Leu Ser
    290                 295                 300

Gly Thr Ser Met Ala Thr Pro His Val Ala Gly Val Ala Ala Leu Val
305                 310                 315                 320

Lys Ser Arg Tyr Pro Ser Tyr Thr Asn Asn Gln Ile Arg Gln Arg Ile
                325                 330                 335

Asn Gln Thr Ala Thr Tyr Leu Gly Ser Pro Ser Leu Tyr Gly Asn Gly
            340                 345                 350

Leu Val His Ala Gly Arg Ala Thr Gln
        355                 360

<210> SEQ ID NO 2
<211> LENGTH: 268
<212> TYPE: PRT
<213> ORGANISM: Bacillus lentus

<400> SEQUENCE: 2

Gln Thr Val Pro Trp Gly Ile Ser Phe Ile Asn Thr Gln Gln Ala His
  1               5                  10                  15

Asn Arg Gly Ile Phe Gly Asn Gly Ala Arg Val Ala Val Leu Asp Thr
                 20                  25                  30

Gly Ile Ala Ser His Pro Asp Leu Arg Ile Ala Gly Gly Ala Ser Phe
             35                  40                  45

Ile Ser Ser Glu Pro Ser Tyr His Asp Asn Asn Gly His Gly Thr His
     50                  55                  60
```

```
Val Ala Gly Thr Ile Ala Ala Leu Asn Asn Ser Ile Gly Val Leu Gly
 65                  70                  75                  80

Val Arg Pro Ser Ala Asp Leu Tyr Ala Leu Lys Val Leu Asp Arg Asn
             85                  90                  95

Gly Ser Gly Ser Leu Ala Ser Val Ala Gln Gly Ile Glu Trp Ala Ile
            100                 105                 110

Asn Asn Asn Met His Ile Ile Asn Met Ser Leu Gly Ser Thr Ser Gly
        115                 120                 125

Ser Ser Thr Leu Glu Leu Ala Val Asn Arg Ala Asn Asn Ala Gly Ile
    130                 135                 140

Leu Leu Val Gly Ala Ala Gly Asn Thr Gly Arg Gln Gly Val Asn Tyr
145                 150                 155                 160

Pro Ala Arg Tyr Ser Gly Val Met Ala Val Ala Ala Val Asp Gln Asn
                165                 170                 175

Gly Gln Arg Ala Ser Phe Ser Thr Tyr Gly Pro Glu Ile Glu Ile Ser
            180                 185                 190

Ala Pro Gly Val Asn Val Asn Ser Thr Tyr Thr Gly Asn Arg Tyr Val
        195                 200                 205

Ser Leu Ser Gly Thr Ser Met Ala Thr Pro His Val Ala Gly Val Ala
    210                 215                 220

Ala Leu Val Lys Ser Arg Tyr Pro Ser Tyr Thr Asn Asn Gln Ile Arg
225                 230                 235                 240

Gln Arg Ile Asn Gln Thr Ala Thr Tyr Leu Gly Ser Pro Ser Leu Tyr
                245                 250                 255

Gly Asn Gly Leu Val His Ala Gly Arg Ala Thr Gln
            260                 265

<210> SEQ ID NO 3
<211> LENGTH: 1086
<212> TYPE: DNA
<213> ORGANISM: Bacillus lentus

<400> SEQUENCE: 3
atgagacaaa gtctaaaagt tatggttttg tcaacagtgg cattgctttt catggcaaac      60
ccagcagcag caggcgggga gaaaaaggaa tatttgattg tcgtcgaacc tgaagaagtt     120
tctgctcaga gtgtcgaaga aagttatgat gtggacgtca tccatgaatt tgaagagatt     180
ccagtcattc atgcagaact aactaaaaaa gaattgaaaa aattaaagaa agatccgaac     240
gtaaaagcca tcgaagagaa tgcagaagta accatcagtc aaacggttcc ttggggaatt     300
tcattcatta atacgcagca agcgcacaac cgcggtattt ttggtaacgg tgctcgagtc     360
gctgtccttg ataca ggaat tgcttcacac ccagacttac gaattgcagg gggagcgagc     420
tttatttcaa gcgagccttc ctatcatgac aataacggac acggaactca cgtggctggt     480
acaatcgctg cgttaaacaa ttcaatcggt gtgcttggtg tacgaccatc ggctgacttg     540
tacgctctca agttcttga tcggaatgga agtggttcgc ttgcttctgt agctcaagga     600
atcgaatggg caattaacaa caacatgcac attattaata tgagccttgg aagcacgagt     660
ggttctagca cgttagagtt agctgtcaac cgagcaaaca atgctggtat tctcttagta     720
ggggcagcag gtaatacggg tagacaagga gttaactatc ctgctagata ctctggtgtt     780
atggcggttg cagcagttga tcaaaatggt caacgcgcaa gcttctctac gtatggccca     840
gaaattgaaa tttctgcacc tggtgtcaac gtaaacagca cgtacacagg caatcgttac     900
gtatcgcttt ctggaacatc tatggcaaca ccacacgttg ctggagttgc tgcacttgtg     960
```
aagagcagat atcctagcta tacgaacaac caaattcgcc agcgtattaa tcaaacagca    1020
acgtatctag gttctcctag cctttatggc aatggattag tacatgctgg acgtgcaaca    1080
caataa                                                                1086

<210> SEQ ID NO 4
<211> LENGTH: 24
<212> TYPE: DNA
<213> ORGANISM: Hepatitis C virus

<400> SEQUENCE: 4
gcagaaagcg tctagccatg gcgt                                            24

<210> SEQ ID NO 5
<211> LENGTH: 24
<212> TYPE: DNA
<213> ORGANISM: Hepatitis C virus
<220> FEATURE:
<221> NAME/KEY: modified_base
<222> LOCATION: (1)
<223> OTHER INFORMATION: Biotin derivatization

<400> SEQUENCE: 5
ctcgcaagca ccctatcagg cagt                                            24

<210> SEQ ID NO 6
<211> LENGTH: 21
<212> TYPE: DNA
<213> ORGANISM: Hepatitis C virus
<220> FEATURE:
<221> NAME/KEY: modified_base
<222> LOCATION: (1)
<223> OTHER INFORMATION: Ruthenium3+-(tris-bipyridyl)-derivatisation

<400> SEQUENCE: 6
gtcgtgcagc ctccaggacc c                                               21

<210> SEQ ID NO 7
<211> LENGTH: 30
<212> TYPE: DNA
<213> ORGANISM: Human immunodeficiency virus
<220> FEATURE:
<221> NAME/KEY: modified_base
<222> LOCATION: (1)
<223> OTHER INFORMATION: Biotin derivatization

<400> SEQUENCE: 7
agttggagga catcaagcag ccatgcaaat                                      30

<210> SEQ ID NO 8
<211> LENGTH: 27
<212> TYPE: DNA
<213> ORGANISM: Human immunodeficiency virus
<220> FEATURE:
<221> NAME/KEY: modified_base
<222> LOCATION: (1)
<223> OTHER INFORMATION: Biotin derivatization

<400> SEQUENCE: 8
tgctatgtca gttccccttg gttctct                                         27

<210> SEQ ID NO 9
<211> LENGTH: 20
<212> TYPE: DNA
<213> ORGANISM: Human immunodeficiency virus
<220> FEATURE:

```
<221> NAME/KEY: modified_base
<222> LOCATION: (1)
<223> OTHER INFORMATION: Ruthenium3+-(tris-bipyridyl)-derivatisation

<400> SEQUENCE: 9
atcaatgagg aagctgcaga                                             20

<210> SEQ ID NO 10
<211> LENGTH: 18
<212> TYPE: DNA
<213> ORGANISM: Hepatitis B virus

<400> SEQUENCE: 10
ggagtgtgga ttcgcact                                               18

<210> SEQ ID NO 11
<211> LENGTH: 18
<212> TYPE: DNA
<213> ORGANISM: Hepatitis B virus
<220> FEATURE:
<221> NAME/KEY: modified_base
<222> LOCATION: (1)
<223> OTHER INFORMATION: Biotin derivatization

<400> SEQUENCE: 11
tgagatcttc tgcgacgc                                               18

<210> SEQ ID NO 12
<211> LENGTH: 18
<212> TYPE: DNA
<213> ORGANISM: Hepatitis B virus
<220> FEATURE:
<221> NAME/KEY: modified_base
<222> LOCATION: (1)
<223> OTHER INFORMATION: Ruthenium3+-(tris-bipyridyl)-derivatisation

<400> SEQUENCE: 12
agaccaccaa atgccct                                                18
```

METHODS FOR THE ANALYSIS OF NON-PROTEINACEOUS COMPONENTS USING A PROTEASE FROM A BACILLUS STRAIN

CROSS-REFERENCE TO RELATED APPLICATIONS

This application claims the benefit of priority under 35 U.S.C. §119 of foreign applications EP Application No. 00123728-8, filed Oct. 31, 2000, and EP Application No. 01106308-8, filed Mar. 15, 2001, the contents of which are hereby incorporated by reference in their entireties.

This invention relates to a method for the analysis of a (at least one) target non-proteinaceous component of a mixture of non-proteinaceous and proteinaceous components derived from a biological sample using a protease from a Bacillus strain. The invention further relates to a method for the analysis of a (at least one) target nucleic acid component of a mixture of non-proteinaceous components, which comprise nucleic acids, and proteinaceous components whereby the mixture is derived from a biological sample comprising the steps of incubating the mixture with a (at least one) protease from a Bacillus strain, optionally amplifying the (at least one) target nucleic acid component, and determining or detecting the (at least one) target nucleic acid component.

BACKGROUND OF THE INVENTION

Many biological substances, especially nucleic acids, present special challenges in terms of isolating them from their natural environment. On the one hand, they are often present in very small concentrations and, on the other hand, they are often found in the presence of many other solid and dissolved substances e.g. after lysis of cells. This makes them difficult to isolate or to measure, in particular in biospecific assays which allow the detection of specific analytes, e.g. nucleic acids, or specific analyte properties and play a major role in the field of diagnostics and bioanalytics in research and development. Examples for biospecific assays are hybridisation assays, immuno assays and receptor-ligand assays. Hybridisation assays use the specific base-pairing for the molecular detection of nucleic acid analytes e.g. RNA and DNA. Hence, oligonucleotide probes with a length of 18 to 20 nucleotides may enable the specific recognition of a selected complementary sequence e.g. in the human genome. Another assay which entails the selective binding of two oligonucleotide primers is the polymerase chain reaction (PCR) described in U.S. Pat. No. 4,683,195. This method allows the selective amplification of a specific nucleic acid region to detectable levels by a thermostable polymerase in the presence of desoxynucleotide triphosphates in several cycles.

As described above, before the biological substances may be analysed in one of the above-mentioned assays or used for other processes, it has to be isolated or purified from biological samples containing complex mixtures of different components as e.g. proteinaceous and non-proteinaceous components. Often, for the first steps, processes are used which allow the enrichment of the component of interest, e.g. the non-proteinaceous material such as nucleic acids. Frequently, these are contained in a bacterial cell, a fungal cell, a viral particle, or the cell of a more complex organism, such as a human blood cell or a plant cell. The component of interest can also be called a "target component".

To release the contents of said cells or particles, they may be treated with enzymes or with chemicals to dissolve, degrade or denature the cellular walls of such organisms. This process is commonly referred to as lysis. The resulting solution containing such lysed material is referred to as lysate. A problem often encountered during the lysis is that other enzymes degrading the non-proteinaceous component of interest, e.g. desoxyribonucleases or ribonucleases degrading nucleic acids, come into contact with the component of interest during lysis. These degrading enzymes may also be present outside the cells or may have been spatially separated in different cellular compartments before the lysis and come now into contact with the component of interest. Other components released during this process may be e.g. endotoxins belonging to the family of lipopolysaccharides which are toxic to cells and can cause problems for products intended to be used in human or animal therapy.

There are a variety of means to tackle this problem mentioned-above. It is common to use chaotropic agents as e.g. guanidinium thiocyanate or anionic, cationic, zwitterionic or non-ionic detergents when nucleic acids are intended to be set free. It is also an advantage to use proteases which rapidly degrade these enzymes or unwanted proteins. However, this may produce another problem as the said substances or enzymes can interfere with reagents or components in subsequent steps.

Enzymes which can be advantageously used in such lysis or sample preparation processes mentioned-above are enzymes which cleave the amide linkages in protein substrates and which are classified as proteases, or (interchangeably) peptidases (See Walsh, 1979, Enzymatic Reaction Mechanisms. W. H. Freeman and Company, San Francisco, Chapter 3). Proteases which have been used in the prior art are e.g. alkaline proteases (WO98/04730) or acid proteases (U.S. Pat. No. 5,386,024). The protease which is widely used in the prior art for sample preparation for the isolation of nucleic acids is proteinase K from *Tritirachium album* (see e.g. Sambrook et al., 1989) which is active around neutral pH and belongs to a family of proteases known to the person skilled in the art as subtilisins. A subtilisin is a serine protease produced by Gram-positive bacteria or fungi.

Bacteria of the Bacillus species secrete two extracellular species of protease, a neutral or metalloprotease, and an alkaline protease which is functionally a serine endopeptidase, referred to as subtilisin. A serine protease is an enzyme which catalyzes the hydrolysis of peptide bonds, in which there is an essential serine residue at the active site (White, Handler, and Smith, 1973 "Principles of Biochemistry," Fifth Edition, McGraw-Hill Book Company, N.Y., pp. 271–272). The serine proteases have molecular weights in the 25,000 to 30,000 Da (Dalton) range. They hydrolyze simple terminal esters and are similar in activity to eukaryotic chymotrypsin, also a serine protease. The alternative term, alkaline protease, reflects the high pH optimum of the serine proteases, from pH 9.0 to 11.0 (for review, see Priest, 1977, Bacteriological Rev. 41: 711–753).

A wide variety of subtilisins have been identified (see e.g. Kurihara et al., 1972, J. Biol. Chem. 247: 5629–563 1; Stahl and Ferrari, 1984, J. Bacteriol. 158: 411–418; Vasantha et al., 1984, J. Bacteriol. 159: 811–819, Jacobs et al., 1985, Nucl. Acids Res. 13: 8913–8926; Nedkov et al., 1985, Biol. Chem. Hoppe-Seyler 366: 421–430; Svendsen et al., 1986, FEBS Lett 196: 228–232; Meloun et al., 1985, FEBS. Lett. 183: 195–200) including proteinase K from Tritirachium album (Jany and Mayer, 1985, Biol. Chem. Hoppe-Seyler 366: 584–492). Subtilisins are well characterized by their primary as well as by their tertiary structure (see e.g. Kraut, 1977, Ann. Rev. Biochem. 46: 331–358; Kurihara et al., 1972, J. Biol. Chem. 247: 5629–5631; Stahl and Ferrari, 1984, J. Bacteriol. 158: 411–418; Vasantha et al., 1984, J. Bacteriol. 159: 811–819; Jacobs et al., 1985, Nucl. Acids Res. 13: 8913–8926; Nedkov et al., 1985, Biol. Chem. Hoppe-Seyler 366: 421–430; Svendsen et al., 1986, FEBS Lett. 196: 228–232; Meloun et al., 1985, FEBS Lett. 183: 195–200; Jany and Mayer, 1985, Biol. Chem. Hoppe-Seyler 366: 485–492).

In connection with this invention the amino acid and DNA sequences of two further serine proteases are of particular interest. These proteases were derived from two Bacillus lentus variants, 147 and 309, which have been deposited with NCIB and designated the accession Nos. NCIB 10147 and NCIB 10309, respectively (see WO89/06279 and U.S. Pat. No. 3,723,250). For convenience the proteases produced by these strains are designated subtilisin 147 and subtilisin 309, respectively, and the genes encoding these proteins are referred to as the subtilisin 147 and 309 genes. The disclosure of these sequences can be found in WO89/06279. The equivalents thereto are EP396608 and U.S. Pat. No. 5,741,694. Subtilisins have found much utility in industry, particularly detergent formulations used for the washing of clothes.

In the next steps of the sample preparation which follow on the lysis step, the component of interest is further enriched. If the non-proteinaceous components of interest are e.g. nucleic acids, they are normally extracted from the complex lysis mixtures before they are used in a probe-based assay.

There are several methods for the extraction of nucleic acids:

sequence-dependent or biospecific methods as e.g.:
  affinity chromatography
  hybridisation to immobilised probes
sequence-independent or physico-chemical methods as e.g.:
  liquid-liquid extraction with e.g. phenol-chloroform
  precipitation with e.g. pure ethanol
  extraction with filter paper
  extraction with micelle-forming agents as cetyl-trimethyl-ammonium-bromide
  binding to immobilised, intercalating dyes, e.g. acridine derivatives
  adsorption to silica gel or diatomic earths
  adsorption to magnetic glass particles (MGP) or organo silane particles under chaotropic conditions Particularly interesting for extraction purposes is the adsorption of nucleic acids to a glass surface although other surfaces are possible. Many procedures for isolating nucleic acids from their natural environment have been proposed in recent years by the use of their binding behavior to glass surfaces.

As mentioned above, the protease which is widely used in the prior art for sample preparation for the isolation of nucleic acids is proteinase K from *Tritirachium album*. However, this protease has the disadvantage that the production is relatively expensive. Further, proteinase K is disadvantageous in methods using magnetic glass particles for the nucleic acid isolation from EDTA, heparin or citrate blood plasma, as the particles will often stick to one another. This is very disadvantageous for automated processes used for the analysis of a very large number of samples.

Therefore, it was an object of the present invention to provide a new method for the analysis of target non-proteinaceous components, in particular nucleic acids, using a protease which is relatively cheap, has constant quality and can be used in a variety of processes. Preferably it should be possible to use it for the analyis of a (at least one) target nucleic acid component from a variety of different matrices e.g. EDTA, citrate, or heparin blood plasma or blood serum. This method should be particularly suitable in automated processes. Ideally the protease would be also very active in the presence of chaotropic agents frequently used in the processes for the purification of nucleic acids.

This problem was solved by the findings of the present invention which is related to a method for the analysis of a (at least one) target non-proteinaceous component of a mixture of non-proteinaceous and proteinaceous components derived from a biological sample comprising the step of incubating the mixture with a (at least one) protease having an amino acid sequence which is at least 80% identical to the amino acid sequence of the protease subtilisin 147 from Bacillus lentus. As can be seen from the example, the protease is very active in the presence of chaotropic agents or equally active for the digestion of citrate or EDTA blood plasma. This could not be foreseen from the prior art.

BRIEF SUMMARY OF THE INVENTION

In summary, this invention relates to a method for the analysis of a (at least one) target non-proteinaceous component of a mixture of non-proteinaceous and proteinaceous components derived from a biological sample using a protease from a Bacillus strain. The invention further relates to a method for the analysis of a (at least one) target nucleic acid component of a mixture of non-proteinaceous components, which comprise nucleic acids, and proteinaceous components whereby the mixture is derived from a biological sample comprising the steps of incubating the mixture with a (at least one) protease having an amino acid sequence which is at least 80% identical to the amino acid sequence of the protease subtilisin 147 from Bacillus lentus, optionally amplifying the (at least one) target nucleic acid component, and determining or detecting the (at least one) target nucleic acid component. Optionally, the nucleic acids and the (at least one) target nucleic acid component are bound to a material with an affinity thereto, optionally washed and optionally released from the material with an affinity thereto, whereby the material with an affinity to nucleic acids and the (at least one) target nucleic acid component comprises a material with a silica surface, in particular magnetic glass particles. The invention is further related to the use of a protease according to the invention in diagnostics, research and bioanalytics e.g. for the purification of nucleic acids, for the analysis of a (at least one) target non-proteinaceous component of a mixture of non-proteinaceous and proteinaceous components derived from a biological sample, for the enrichment of a (at least one) target non-proteinaceous component of a mixture of non-proteinaceous and proteinaceous components derived from a biological sample or for the purification or isolation of a (at least one) target non-proteinaceous component of a mixture of non-proteinaceous and proteinaceous components derived from a biological sample. The invention is also related to a kit comprising the protease according to the invention and the use of a kit according to the invention in diagnostics and/or for the purification of nucleic acids. The invention will be described in more detail below.

BRIEF DESCRIPTION OF THE DRAWINGS

Figure Legends

DETAILED DESCRIPTION OF THE INVENTION

Figure 1A:
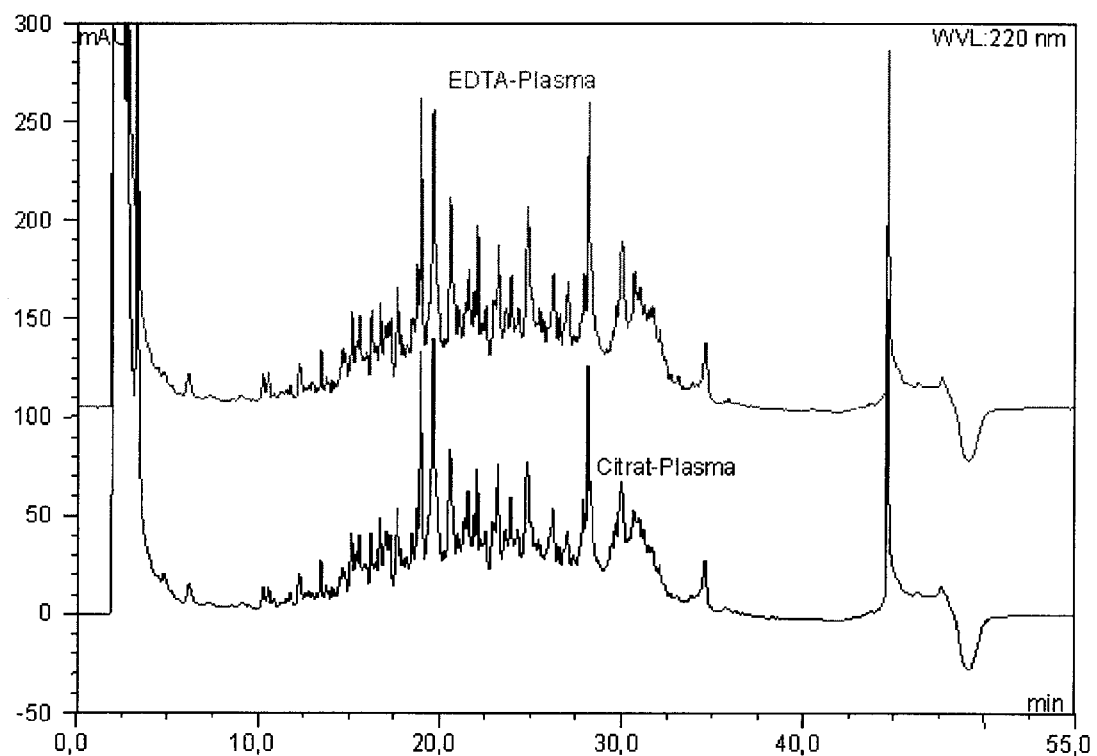
FIG. 1a: Comparison of the digestion of EDTA plasma versus citrate plasma with Esperase as analyzed by high pressure liquid chromatography

It is one embodiment of this invention to provide a method for the analysis of a (at least one) target non-proteinaceous component of a mixture of non-proteinaceous and proteinaceous components derived from a biological sample comprising the step of incubating the mixture with a (at least one) protease having an amino acid sequence which is at least 80% identical to the amino acid sequence of the protease subtilisin 147 from Bacillus lentus. The term "derived" means that a biological sample is manipulated or treated in order to create a mixture of non-proteinaceous and proteinaceous components which are originally contained in the biological sample. From this mixture it should be possible to analyse, isolate, enrich or purify specific non-proteinaceous components. The term "analysis" shall mean that the presence or the amount of the target non-proteinaceous component is investigated, i.e. the target non-proteinaceous component is detected or determined or the amount thereof is determined. Manipulation or treatment steps include chemical or physical manipulation steps which are known to the expert in the field. More specifically, this can be done by lysing the biological sample. Biological samples are samples which are taken from a plant or an animal (including a human being) and are solid or liquid. Specific examples are described in more detail below.

In a further embodiment of the invention, the method has further steps after the incubation as binding the (at least one) target non-proteinaceous component to a material with an affinity thereto, optionally washing and optionally releasing the (at least one) target non-proteinaceous component from the material with an affinity thereto. Afterwards, the (at least one) target non-proteinaceous component may be determined or detected by standard analytical methods known to the person skilled in the art and described e.g. in Sambrook et al. (1989), Molecular Cloning, Cold Spring Harbor University Press, New York, N.Y., USA or in "Bioanalytik", Lottspeich and Zorbas (eds.), 1$^{st}$ edition 1998, Spektrum Akademischer Verlag, Heidelberg, Berlin, Germany. Preferably, the amount of the target non-proteinaceous component is determined with the methods described therein. The method according to the invention is preferably used in research, bioanalytics in particular in diagnostics or in diagnostic investigations in medicine, i.e. in methods that are used to determine the cause of an illness or disorder in humans or in animals.

Therefore, a preferred embodiment of the invention is a method for the analysis of a (at least one) target non-proteinaceous component of a mixture of non-proteinaceous and proteinaceous components derived from a biological sample comprising the steps of:
a) incubating the mixture with a (at least one) protease according to the invention,
b) binding the (at least one) target non-proteinaceous component to a material with an affinity thereto,
c) optionally washing and optionally releasing the (at least one) target non-proteinaceous component from the material with an affinity thereto, and
d) determining or detecting the (at least one) target non-proteinaceous component.

In the most preferred embodiment, the step c) is not optional, i.e. that the bound (at least one) target non-proteinaceous component is washed and released from the material with an affinity thereto. Preferably the amount of the target non-proteinaceous component is determined.

The protease according to the invention degrades the proteinaceous components, i.e. the components containing peptide bonds which shall be hydrolyzed if it is of interest to enrich, isolate or purify the (at least one) target non-proteinaceous component of the biological sample. The protease according to the present invention may be added in solid form e.g. as a tablet or a powder or in a dissolved form in a buffered or unbuffered solution in a similar manner as described for proteinase K.

For the purpose of this invention, the term "esperase" shall mean the protease according to the invention, i.e. the protease subtilisin 147 derived from the Bacillus lentus variant 147, which was deposited with NCIB under accession No. NCIB 10147. The amino acid sequence SEQ ID NO 1 is the full length amino acid sequence of the protease subtilisin 147 (or esperase) including a signal sequence which is removed after secretion by the action of proteases. A signal sequence is a sequence that directs secretion of an expressed protein from the host cell and is proteolytically removed after secretion. The SEQ ID NO 2 is the sequence of esperase without signal sequence. The term "esperase" shall also comprise those proteolytical derivatives of SEQ ID NO 1 which might be generated by incomplete or inexact processing of the signal sequence and which still have proteolytic activity including those with a lower activity than that of the correctly processed esperase. The amino acid sequence of the protein may be encoded by the subtilisin 147 gene, i.e. the nucleotide sequence SEQ ID NO 3, by parts thereof or a degenerated version thereof. Degenerated sequences are degenerated within the meaning of the genetic code in that an unlimited number of nucleotides are replaced by other nucleotides without resulting in a change of the amino acid sequence originally encoded.

According to the present invention the term "proteinaceous material" is meant to describe material that contains a (at least one) peptide bond, therefore "proteinaceous material" is preferably a composition of matter containing a (at least one) protein with natural amino acids. Most of these peptide bonds may be hydrolyzed by the protease according to the present invention depending on the chemical nature of the neighboring chemical groups (or amino acids) and the accessibility of the peptide bond, i.e. the proteinaceous material is a substrate to the protease according to the invention. In consequence, the term "non-proteinaceous material" is meant to describe material that does not contain a peptide bond and is not substrate to the protease according to the present invention.

The protease subtilisin 147 from Bacillus lentus is commercially available e.g. from Roche Molecular Biochemicals, Mannheim, Germany, or from Novo Nordisk, Denmark. In certain embodiments of the invention, the mixture of proteinaceous components and target non-proteinaceous components can be incubated with commercially available protease without any purification or preparation of the protease. In other embodiments of the invention, the comercially available protease can be prepared or purified to remove contaminants. For example, the protease can be dialyzed against a buffer that is compatible with the mixture. A solution comprising the commercially availiable protease can also be filtered or sterilized. In addition, the commercially available protease can optionally be purified or partially purified to remove contaminants such as nucleases according to protein purification techniques known to those of skill in the art. For instance, the commercially available protease can be partially purified by ammonium sulfate precipitation and/or by chromatography methods such as heparin-sepharose ff chromatography. Preferred methods for the preparation of commercially available subtilisin 147 are described in the examples below.

Another possibility to obtain this protease is to isolate the gene from the deposited microorganism or to synthesize the gene coding for that protease according to standard methodology see e.g. Sambrook et al. (1989), Molecular Cloning, Cold Spring Harbor University Press, New York, N.Y., USA. The amino acid sequence of the pro-protein comprising a signal sequence (SEQ ID NO 1), the amino acid sequence of the secreted protease (SEQ ID NO 2) and the DNA sequence (see SEQ ID NO 3) of this protein are known from WO89/06279, EP 396 608 and WO98/20115. The major form of the secreted protein is encoded by the nucleotides 280 to 1083 of SEQ ID NO 3, i.e. the signal peptide is encoded by the nucleotides 1 to 279 of SEQ ID NO 3. The isolation of the microorganism is described in U.S. Pat. No. 3,723,250. The isolated strain is deposited under NCIB 10147. Custom gene synthesis can be performed by example by Operon Technologies, Alameda, Calif., USA, recently acquired by Qiagen, Germany. Using standard methodology the person skilled in the art can construct an expression vector, express the gene product and isolate the protein essentially as described in WO89/06279 or WO98/20115 which shall be incorporated herein by reference.

With this information in hand, the expert in the field can also construct and express a gene coding for a protease with an amino acid sequence with 80% identity to the amino acid sequence of subtilisin 147 by substituting various amino acids. Therefor, he uses standard methodology as described in Sambrook et al. (1989), Molecular Cloning, Cold Spring Harbor University Press, New York, N.Y., USA or methodology as described in WO89/06279 or WO98/20115. The tests for the proteolytical activity are described in these two international applications or in this invention.

In further embodiments, a method according to the invention is disclosed in which a protease is used with an amino acid sequence which is identical (100% identical) to the amino acid sequence of the protease subtilisin 147 from Bacillus lentus. In a further embodiment, a method according to the invention is disclosed characterized in that the amino acid sequence of protease is the amino acid sequence SEQ ID NO 1, a proteolytical derivative thereof having protease activity or the amino acid sequence SEQ ID NO 2. In still another embodiment of the invention, a method according to the invention is disclosed characterized in that the amino acid sequence of the protease according to the invention is encoded by the nucleic acid sequence SEQ ID NO 3, a part thereof coding for an active protease according to the invention or a degenerated version of the nucleic acid sequence SEQ ID NO 3. The invention contemplates derivatives of the DNA sequence SEQ ID NO 3 which have been altered by substitutions, deletions and additions that provide for functionally equivalent molecules. For example, due to the degeneracy of nucleotide coding sequences, other DNA sequences which encode substantially the same amino acid sequence as depicted in SEQ ID NO 1 or 2 can be used in the practice of this invention. Further, amino acid sequences can be used which have amino acid substitutions at positions where amino acids of the same group, e.g. polar or hydrophobic have been exchanged for one another.

In an embodiment of the invention the biological sample is intended to comprise viruses or bacterial cells, as well as isolated cells from multicellular organisms as e.g. human and animal cells such as leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In a preferred embodiment of the invention the biological sample is a fluid from the human or animal body, preferably the biological sample is blood, blood plasma, blood serum or urine. The blood plasma is preferably EDTA, heparin or citrate blood plasma. In an embodiment of the invention the biological sample comprises bacterial cells, eukaryotic cells, viruses or mixtures thereof.

The biological sample can also be of a type used for environmental analysis, food analysis or molecular biology research, e.g. from bacterial cultures, phage lysates. In certain cases the sample can be used without pretreatment in the method according to the invention. In many cases, however, the sample should be lysed using an appropriate method, releasing the biological substances contained in the sample thereby creating a mixture of proteinaceous and non-proteinaceous components derived from the biological sample. Procedures for lysing samples are known by the expert and can be chemical, enzymatic or physical in nature. A combination of these procedures is applicable as well. For instance, lysis can be performed using ultrasound, high pressure, by shear forces, using alkali, detergents or chaotropic saline solutions, or by means of proteases or lipases. With regard for the lysis procedure to obtain nucleic acids, special reference is made to Sambrook et al.: Molecular Cloning, A Laboratory Manual, 2nd Addition, Cold Spring Harbour Laboratory Press, Cold Spring Harbour, NY, USA, and Ausubel et al.: Current Protocols in Molecular Biology 1987, J. Wiley and Sons, NY, USA.

In still another embodiment of the invention the biological sample comprises a (at least one) glycosylated protein which is partially or fully degraded by the protease according to the invention. Therefore, the invention also contemplates the use of the protease according to the invention for the partial or full degradation of glycosylated proteins, i.e. proteins with covalently attached carbohydrate moieties.

The method according to the invention can also have further steps after the incubation as binding the (at least one) target non-proteinaceous component to a material with an affinity thereto, optionally washing and optionally releasing the (at least one) target non-proteinaceous component from the material with an affinity thereto. Afterwards, the (at least one) target non-proteinaceous component may be determined or detected by standard analytical methods known to the person skilled in the art and described e.g. in Sambrook et al. (1989), Molecular Cloning, Cold Spring Harbor University Press, New York, N.Y., USA or in "Bioanalytik", Lottspeich and Zorbas (eds.), $1^{st}$ edition 1998, Spektrum Akademischer Verlag, Heidelberg, Berlin, Germany.

In order to bind the (at least one) target non-proteinaceous component to a material with an affinity thereto, the mixture of non-proteinaceous and proteinaceous components is brought in contact with the material with an affinity to the (at least one) target non-proteinaceous component under conditions in which the (at least one) target non-proteinaceous component binds to the surface of the material. The conditions for this depend on the type of the (at least one) target non-proteinaceous component involved, but are basically known to the expert in the field. They also depend on the method by which the (at least one) target non-proteinaceous component is bound to the surface. For example, if modified nucleic acids are the target non-proteinaceous components, the binding can take place via the groups of nucleic acids that represent the modification, e.g., biotin via binding with streptavidin-coated surfaces.

If unmodified nucleic acids are the target non-proteinaceous components, a direct binding of the nucleic acids to a material with a silica surface is preferred because among other reasons the nucleic acids do not have to be modified and even native nucleic acids can be bound. These processes are described in detail by various documents. In Proc. Natl. Acad. USA 76, 615–691 (1979), for instance, a procedure for binding nucleic acids from agarose gels in the presence of sodium iodide to ground flint glass is proposed. The purification of plasmid DNA from bacteria on glass dust in the presence of sodium perchlorate is described in Anal. Biochem. 121, 382–387 (1982). In DE-A 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Anal. Biochem. 175, 196–201 (1988). The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples. The use of magnetic particles to immobilize nucleic acids after precipitation by adding salt and ethanol is more advantageous and described e.g. in Anal. Biochem. 201, 166–169 (1992) and PCT GB 91/00212. In this procedure, the nucleic acids are agglutinated along with the magnetic particles. The agglutinate is separated from the original solvent by applying a magnetic field and performing a wash step. After one wash step, the nucleic acids are dissolved in a Tris buffer. This procedure has a disadvantage, however, in that the precipitation is not selective for nucleic acids. Rather, a variety of solid and dissolved substances are agglutinated as well. As a result, this procedure can not be used to remove significant quantities of any inhibitors of specific enzymatic reactions that may be present. Magnetic, porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin. Magnetizable particular adsorbents proved to be very efficient and suitable for automatic sample preparation. Ferrimagnetic and ferromagnetic as well as superparamagnetic pigments are used for this purpose. The most preferred MGPs are those described in WO01/37291.

In detail, the procedure for binding the (at least one) target nucleic acid to glass particles can be described as follows. It is preferably performed in the presence of chaotropic salts with a concentration of between 1 and 8 mol/l, and preferably between 2 and 6 mol/l. Chaotropic salts can be sodium iodide, sodium perchlorate, guanidinium thiocyanate, guanidinium isothiocyanate or guanidinium hydrochloride. Other substances are also possible. The purification effect results from the behavior of DNA or RNA to bind to material with a glass surface under these conditions i.e. in the presence of certain concentration of a chaotropic agent, higher concentrations of organic solvents or under acidic conditions. To bring the sample in contact with the material with an affinity to the (at least one) target non-proteinaceous component, the sample is mixed with the material and incubated for a period of time sufficient for the binding to occur. Experts are usually familiar with the duration of the incubation step from procedures for performing treatment with non-magnetic particles. This step can be optimized by determining the quantity of immobilized biological material on the surface at different points in time. Incubation times of between 10 seconds and 30 minutes can be appropriate for nucleic acids. After incubation, the bound (at least one) target non-proteinaceous component is separated from the liquid. This may be achieved in general by gravity or in the convenient case of nucleic acids bound to magnetic glass particles by separating the material bound to the magnetic particles by applying a magnetic field. For instance, the magnetic particles can be pulled to the wall of the vessel in which incubation was performed. The liquid containing the sample contents that were not bound to the magnetic particles can then be removed. The removal procedure used depends on the type of vessel in which incubation was performed. Suitable steps include removing the liquid via pipetting or aspiration. The material with the bound DNA or RNA may then be washed at least once, preferably with a mixture of 70 volume parts ethanol with 30 volume parts water ("70% Ethanol"). A wash solution is used that does not cause the (at least one) target non-proteinaceous component to be released from the material surface but that washes away the undesired contaminants as thoroughly as possible. This wash step preferably takes place by incubating the material with the bound (at least one) target non-proteinaceous component with the wash solution. The material is preferably resuspended during this step. The contaminated wash solution is preferably removed just as in the step described above for binding the biological material. After the last wash step, the material can be dried briefly in a vacuum, or the fluid can be allowed to evaporate. A pretreatment step using acetone may also be performed. Afterwards, the conditions may be reversed, e.g. the concentration of the chaotropic agent or organic solvent is decreased to elute the DNA or RNA bound to the material. Preferably, the process of separating the magnetic glass particles from the rest of the sample is done by pelleting the immobilized biological material, e.g. by gravity force or by the use of a magnet in the case of magnetic glass particles and removal of the supernatant. Then the magnetic glass particles with the immobilized biological material are resuspended in a solution with no or only a low amount of chaotropic agent and/or organic solvent. Alternatively, the suspension can be diluted with a solution with no or only a low amount of chaotropic agent and/or organic solvent. Buffers of this nature are known from DE 3724442 and Analytical Biochemistry 175, 196–201 (1988). The elution buffers with a low salt content are in particular buffers with a content of less than 0.2 mol/l. In an especially preferred embodiment, the elution buffer contains the substance Tris for buffering purposes. In another special embodiment, the elution buffer is demineralized water. The solution containing purified DNA or RNA can now be used for other reactions.

For washing and binding steps, preferably liquids are used which are suitable for processes in molecular biology, in particular desoxyribonucleic acid (DNA) or ribonucleic acid (RNA) purification processes which make use of the binding of these substances to glass particles under certain conditions. Preferred liquids comprise alcohols and/or ketones or any mixtures thereof with water. Alcohols shall include according to the invention preferably primary, secondary or tertiary alcohols of the general formula R—OH where the R stands for the general formula —(—$CH_2$)$_n$—$CH_3$ with n>=0. However, other alcohols can also be used if they are suitable for molecular biology purposes as e.g. glycerol. Particularly suitable are the alcohols isopropanol, ethanol or mixtures thereof with water, preferably a mixture of 80 volume parts of isopropanol with 20 volume parts of water. In another embodiment of the invention the liquid comprises ketones as e.g. acetone.

The magnetic glass particles used in the present invention may be provided in different formulations. It is possible to provide them in the form of a tablet, as a powder or preferably as a suspension. In a preferred embodiment of the invention these suspensions contain between 5 to 60 mg/ml magnetic glass particles (MGPs). In another embodiment of the invention the silica-containing material is suspended in aqueous buffered solutions which may optionally contain a chaotropic agent in a concentration of between 2 and 8 mol/l, and preferably between 4 and 6 mol/l. Chaotropic salts are sodium iodide, sodium perchlorate, guanidinium thiocyanate, guanidinium isothiocyanate or guanidinium hydrochloride. Other compounds known to the expert in the field are also possible. A chaotropic agent according to the present invention is any chemical substance which disturbs the ordered structure of liquid water and has the effect that DNA or RNA binds to the magnetic glass particles if this agent is present in the DNA or RNA containing solution. It is obvious for the artisan to produce suitable aqueous buffered solutions. Buffer systems which suitable for molecular biology purposes may be found e.g. in Sambrook et al. (1989), Molecular Cloning, Cold Spring Harbor University Press, New York, N.Y., USA. Preferred buffer substances are Tris-(hydroxymethyl)-aminomethane (TRIS), phosphate, N-(2-Hydroxyethyl)piperazine-N'-(2-ethanesulfonic acid) (HEPES), salts thereof or other suitable substances. Additionally, substances may be present which modify the ionic strength of the solution as e.g. NaCl, KCl or $CaCl_2$ or which are metal cation complexing agents as e.g. ethylene-diamine-tetra-acetic acid (EDTA) or the salts thereof. Other biological substances known to the expert in the field may also be present. The method according to the present invention is suitable for the purification of nucleic acids, i.e. RNA or DNA, from complex mixtures with other biological substances containing them. Thereby also mixtures of different nucleic acids may be purified, even mixtures containing a nucleic acid of interest in low abundance. In one embodiment of the invention mixtures of specific nucleic acids are purified, in which the target nucleic acid(s) may be a minor component in terms of concentration (or may be present in low abundance).

The procedure described can be used to isolate native or modified biological material. Native biological material is understood to be material, the structure of which was not irreversibly changed compared with the naturally-occurring biological materials. This does not mean that other components of the sample can not be modified, however. Modified biological materials include materials that do not occur in nature, e.g., nucleic acids that are modified by attaching to them groups that are reactive, detectable or capable of immobilization. An example of this are biotinylated nucleic acids.

After the steps described above, the non-proteinaceous components isolated using the method according to the invention can now be used further as necessary. For instance, they can be used as a substrate for various enzymatic reactions. When nucleic acids are involved, they can be used for sequencing, radioactive or non-radioactive labelling, amplification of one or more of the sequences they contain, transcription, hybridization with labelled probe nucleic acids, translation or ligation. Therefore, in a more preferred embodiment of the invention the method comprises the step of releasing the bound (at least one) target non-proteinaceous component from the material with an affinity thereto. If desired, the (at least one) target non-proteinaceous component purified in this manner can be separated from the material as described above.

In a preferred embodiment of the invention the method comprises the step of detecting or determining a (at least one) target non-proteinaceous component. A preferred embodiment of the invention are therefore the above-described purification method followed by a determination or detection step or purification methods followed by an amplification and determination or detection step. In the case of nucleic acids, the target nucleic acid or nucleic acids of interest may be contained in a matrix of non-target nucleic acids, and may even be a minor component in said mixture of specific nucleic acids. Suitable DNA detection methods are known to the expert in the field and are described in standard textbooks as Sambrook et al.: Molecular Cloning, A Laboratory Manual, 2nd Addition, Cold Spring Harbour Laboratory Press, Cold Spring Harbour, N.Y. and Ausubel et al.: Current Protocols in Molecular Biology 1987, J. Wiley and Sons, NY. There may be also further purification steps before the DNA detection step is carried out as e.g. a precipitation step. The detection methods may include but are not limited to the binding or intercalating of specific dyes as ethidiumbromide which intercalates into the double-stranded DNA and changes its fluorescence thereafter. The purified DNA may also be separated by electrophoretic methods optionally after a restriction digest and visualized thereafter. There are also probe-based assays which exploit the oligonucleotide hybridisation to specific sequences and subsequent detection of the hybrid. It is also possible to sequence the DNA after further steps known to the expert in the field. Other methods apply a diversity of DNA sequences to a silicon chip to which specific probes are bound and yield a signal when a complementary sequences bind.

In a preferred embodiment of the invention the mixture of non-proteinaceous and proteinaceous components comprises nucleic acids whereby the nucleic acids comprise DNA or RNA or both.

A preferred embodiment of the invention is related to a method for the analysis of a (at least one) target nucleic acid component of a mixture non-proteinaceous components, which comprise nucleic acids, and proteinaceous material derived from a biological sample comprising the steps of a) incubating the mixture with a (at least one) protease having an amino acid sequence which is at least 80% identical to the amino acid sequence of the protease subtilisin 147 from Bacillus lentus, b) optionally amplifying the (at least one) target nucleic acid component, and c) determining or detecting the (at least one) target nucleic acid component.

In a preferred embodiment of the invention, the amount of the target nucleic acid component is determined.

In an embodiment of the invention the amino acid sequence of the protease is identical to the amino acid sequence of the protease subtilisin 147 from Bacillus lentus. In a preferred embodiment of the invention the amino acid sequence of protease is the amino acid sequence SEQ ID NO 1, a proteolytical derivative thereof having protease activity or the amino acid sequence SEQ ID NO 2. In yet another preferred embodiment of the invention the amino acid sequence of the protease according to the invention is encoded by the nucleic acid sequence SEQ ID NO 3, a part thereof or a degenerated version of the nucleic acid sequence SEQ ID NO 3. In still another embodiment of the invention the biological sample is intended to comprise viruses or bacterial cells, as well as isolated cells from multicellular organisms as e.g. human and animal cells such as leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In a preferred embodiment of the invention the biological sample is a fluid from the human or animal body, preferably the biological sample is blood, blood plasma, blood serum or urine. The blood plasma is preferably EDTA, heparin or citrate blood plasma. In an embodiment of the invention the biological sample comprises bacterial cells, eukaryotic cells, viruses or mixtures thereof.

In a preferred embodiment of the invention the mixture of nucleic acids and proteinaceous material comprises desoxyribonucleic acid (DNA) or ribonucleic acid (RNA) or both, preferably the DNA or RNA or both is derived from a (at least one) virus or a (at least one) microorganism. The virus can be hepatitis A virus (HAV), hepatitis B virus (HBV), hepatitis C virus (HCV), the human immunodeficiency virus (HIV), the human papilloma virus (HPV) or parvovirus B19.

In a preferred embodiment of the invention a (at least one) target nucleic acid component and the other nucleic acids are purified essentially as described above. Then the (at least one) target nucleic acid component is further manipulated and detected, i.e. it is amplified with the polymerase chain reaction which specifically amplifies target sequences to detectable amounts. Other possible amplification reactions are the ligase Chain Reaction (LCR, Wu and Wallace, 1989, Genomics 4:560–569 and Barany, 1991, Proc. Natl. Acad. Sci. USA 88:189–193); Polymerase Ligase Chain Reaction (Barany, 1991, PCR Methods and Applic. 1:5–16); Gap-LCR (PCT Patent Publication No. WO 90/01069); Repair Chain Reaction (European Patent Publication No. 439,182 A2), 3SR (Kwoh et al., 1989, Proc. Natl. Acad. Sci. USA 86:1173–1177; Guatelli et al., 1990, Proc. Natl. Acad. Sci. USA 87:1874–1878; PCT Patent Publication No. WO 92/0880A), and NASBA (U.S. Pat. No. 5,130,238). Further, there are strand displacement amplification (SDA), transcription mediated amplification (TMA), and Qβ-amplification (for a review see e.g. Whelen and Persing (1996). Annu. Rev. Microbiol. 50, 349–373; Abramson and Myers, 1993, Current Opinion in Biotechnology 4:41–47).

A particularly preferred detection method is the TAQMAN® method disclosed in WO92/02638 and the corresponding US patents U.S. Pat. No. 5,210,015, U.S. Pat. No. 5,804,375, U.S. Pat. No. 5,487,972. This method exploits the exonuclease activity of a polymerase to generate a signal. In detail, the (at least one) target nucleic acid component is detected by a process comprising contacting the sample with an oligonucleotide containing a sequence complementary to a region of the target nucleic acid component and a labeled oligonucleotide containing a sequence complementary to a second region of the of the same target nucleic acid component sequence strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. TAQMAN® technology eliminates the need for a solid phase bound reaction complex to be formed and made detectable. In more general terms, a procedure for the purification of a (at least one) target nucleic acid component followed by a detection step is disclosed wherein the amplification and/or detection reaction is a homogeneous solution-phase.

In another preferred embodiment of the invention the nucleic acids including the (at least one) target nucleic acid component are bound to a material with an affinity thereto before they are optionally amplified or determined or detected. After binding they are optionally washed and optionally released from the material with an affinity thereto essentially as described above. Therefore, a preferred embodiment of the invention is related to a method for the analysis of a (at least one) target nucleic acid component of a mixture non-proteinaceous components, which comprise nucleic acids, and proteinaceous material derived from a biological sample comprising the steps of a) incubating the mixture with a (at least one) protease according to the invention b) binding the (at least one) target non-proteinaceous component to a material with an affinity thereto, c) optionally washing and optionally releasing the (at least one) target nucleic acid component from the material with an affinity thereto, d) optionally amplifying the (at least one) target nucleic acid component, and e) determining or detecting the (at least one) target nucleic acid component.

In the most preferred embodiment, the steps c) and d) are not optional, i.e. that the bound (at least one) target nucleic acid component is washed and released from the material with an affinity thereto and the (at least one) target nucleic acid component is amplified before it is determined or detected. Preferably the amount of the target nucleic acid component is determined.

The material with an affinity to nucleic acids and the (at least one) target nucleic acid component comprises a material with a silica surface, preferably the material with a silica surface is a glass, most preferably the material with an affinity to nucleic acids is a composition comprising magnetic glass particles. The steps are performed essentially as already describe above. In summary, magnetic glass particles are added to the lysis mixture comprising the nucleic acids including the (at least one) target nucleic acid component. After a suitable period of time for adsorption to take place—which can be optimized by mechanical agitation— the particles are separated from the surrounding fluid that contains additional components that are not to be detected. This is performed preferably by applying a magnetic field by placing a magnet against the vessel wall and removing the remaining liquid from the tube. To remove further contaminants that may still be present, a wash step is preferably performed with a fluid that does not cause the nucleic acids and the (at least one) target nucleic acid component to be released from the glass surface. An elution buffer having reagent conditions under which the nucleic acids and the (at least one) target nucleic acid component are not bound to the glass surface and are eluted is added to remove the nucleic acids including the (at least one) target nucleic acid component from the glass surface. These conditions are low salt conditions in particular. Depending on the intended further use of the nucleic acids and the (at least one) target nucleic acid component, the fluid can now be separated from the particles and processed further. This separation step is preferably performed via application of a magnetic field so that the particles are separated from the eluate. The most preferred magnetic glass particles for this method are described in WO01/37291.

Preferably the method according to the invention is used for diagnostic analysis or bioanalytics.

In a preferred embodiment of the invention the protease according to the invention is used in research, bioanalytics or diagnostics. In further preferred embodiments the protease according to the invention is used for the analysis of a (at least one) target non-proteinaceous component of a mixture of non-proteinaceous and proteinaceous components derived from a biological sample, for the enrichment of a (at least one) target non-proteinaceous component of a mixture of non-proteinaceous and proteinaceous components derived from a biological sample or for the purification or isolation of a (at least one) target non-proteinaceous component of a mixture of non-proteinaceous and proteinaceous components derived from a biological sample. Preferably the (at least one) target non-proteinaceous component is a nucleic acid, preferably from a virus or a microorganism, or the mixture of non-proteinaceous and proteinaceous components comprises nucleic acids. Preferred viruses are hepatitis B virus, hepatitis C virus or the human immunodeficiency virus or the other viruses described above.

The invention further contemplates a kit of parts characterized in that it contains a (at least one) protease having an amino acid sequence, which is at least 80% identical to the amino acid sequence of the protease subtilisin 147 from Bacillus lentus. In another embodiment of the invention the amino acid sequence of the protease is identical to the amino acid sequence of the protease subtilisin 147 from Bacillus lentus. In a preferred embodiment of the invention the amino acid sequence of protease is the amino acid sequence SEQ ID NO 1, a proteolytical derivative thereof having protease activity or the amino acid sequence SEQ ID NO 2, preferably the amino acid sequence of the protease according to the invention is encoded by the nucleic acid sequence SEQ ID NO 3, a part thereof coding for an active protease or a degenerated version of the nucleic acid sequence SEQ ID NO 3. Such kits known in the art further comprise plastics ware which can be used during the sample preparation procedure as e.g. microtitre plates in the 96 or 384 well format or just ordinary reaction tubes manufactured e.g. by Eppendorf, Hamburg, Germany and all other reagents for carrying out the method according to the invention. Therefore, the kit can additionally contain a material with an affinity to nucleic acids (and the (at least one) target nucleic acid component), preferably the material with an affinity to nucleic acids (and the (at least one) target nucleic acid component) comprises a material with a silica surface. Preferably, the material with a silica surface is a glass. Most preferably, the material with an affinity to nucleic acids is a composition comprising magnetic glass particles. The kit can further or additionally comprise a lysis buffer containing e.g. chaotropic agents, detergents or alcohols or mixtures thereof which allows the lysis of cells. These components of the kit according to the invention may be provided separately in tubes or storage containers. Depending on the nature of the components, these may be even provided in a single tube or storage container. The kit may further or additionally comprise a washing solution which is suitable for the washing step of the magnetic glass particles when DNA or RNA is bound thereto. This washing solution may contain ethanol and/or chaotropic agents in a buffered solution or solutions with an acidic pH without ethanol and/or chaotropic agents as described above. Often the washing solution or other solutions are provided as stock solutions which have to be diluted before use. The kit may further or additionally comprise an eluent or elution buffer, i.e. a solution or a buffer (e.g. 10 mM Tris, 1 mM EDTA, pH 8.0) or pure water to elute the DNA or RNA bound to the magnetic glass particles. Further, additional reagents or buffered solutions may be present which can be used for the purification process of a nucleic acid, i.e. DNA or RNA.

A preferred embodiment of the present invention is to use the method or the kit of the present invention in automatable methods as e.g. described in WO 99/16781. Automatable method means that the steps of the method are suitable to be carried out with an apparatus or machine capable of operating with little or no external control or influence by a human being. Automatized method means that the steps of the automatable method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. Preferred automatized methods are those which are carried out in a high-throughput format which means that the methods and the used machine or apparatus are optimized for a high-throughput of samples in a short time. In another embodiment of the invention the methods or the kits according to the present invention are used in semi-automatized process which means that some reaction steps may have to be done manually. In a preferred embodiment of the invention, a suspension containing MGPs according to the present invention is taken from a storage container and partial volumes are added to different reaction vessels. Reaction vessels may be reaction tubes made from plastics eventually in mictrotitreplate format contain 96 or 384 or more wells where a reaction can be carried out. However, these vessels may be made from other material e.g. from steel.

In preferred embodiments of the invention the kit according to the invention is used for the purification of nucleic acids in research, bioanalytics or diagnostics. In preferred embodiments according to the invention the kit according to the invention or the method according to the invention is use in a high-throughput format, i.e. in an automatized method which allows the analysis of a high number of different samples in a very short time.

The person skilled in the art knows from the teachings and the example of the present invention how to identify other proteases performing in an equivalent manner as the protease according to the invention, i.e. the protease esperase. Thereby, it is also possible to identify variant or mutant proteins of esperase performing in an equivalent manner to esperase. "Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native esperase due to amino acid deletions, substitutions, or both. "Native sequence" refers to an amino acid or nucleic acid sequence which is identical to a wild-type or native form of a gene or protein.

To find these variant or mutant proteins, he will prepare solutions identical to the reagents and buffers described in Example 1 whereby esperase is used as a standard for the determination of the protease activity. Primarily, the expert in the field will analyze the protease of interest as described in the Chromatographic Analysis of Plasma Protein Digestion Protocol (see Example 3). The protease in question will further be analyzed by its properties in sample preparation with subsequent PCR amplification and detection of the amplified product (see Example 2). Of further interest for comparison with the disclosed enzyme esperase is the investigation of the storage stability (see Example 6) or the evaluation of the enzymatic activity in the presence of chaotropic agents (see Example 5). Taking the results of these investigations into account, the expert in the field can decide whether a protease of interest performs in an equivalent manner as the protease esperase disclosed by the present invention.

A further embodiment of the invention is an aequeous composition of a protease according to the invention, i.e. a protease which is at least 80% identical to the amino acid sequence of the protease subtilisin 147 from Bacillus lentus whereby the composition comprises 10 mM Tris acetate, 5 mM calcium chloride, 5 mM calcium acetate, 1 mM EDTA, 50% (V/V=Volume/Volume) glycerin with a pH value of 5.5. This composition is an ideal storage buffer for esperase (see example 6), The expert skilled in the art is able to modify the composition of the buffer taking the teachings of example 5 into account as long as the protease according to the invention is equally stable in the modified buffer composition. In a further embodiment, the amino acid sequence of the protease in the above-described composition is identical to the amino acid sequence of the protease subtilisin 147 from Bacillus lentus or the amino acid sequence of protease is the amino acid sequence SEQ ID NO 1, a proteolytical derivative thereof having protease activity or the amino acid sequence SEQ ID NO 2. In another embodiment, the amino acid sequence of the protease according to the invention in the above-described composition is encoded by the nucleic acid sequence SEQ ID NO 3, a part thereof or a degenerated version of the nucleic acid sequence SEQ ID NO 3. The composition according to the invention can be used in sample preparation or sample preparation methods, in particular in the methods according to the invention, for the purification of nucleic acids or in diagnostics or diagnostical analysis.

The following examples, references, sequence listing and figures are provided to aid the understanding of the present invention, the true scope of which is set forth in the appended claims. It is understood that modifications can be made in the procedures set forth without departing from the spirit of the invention.

EXAMPLE 1

Reagents and Buffers 1.1 Proteases

The following proteases have been tested for their suitability in the sample preparation process:

| | |
|---|---|
| ALCALASE ® (subtilisin from *Bacillus licheniformis*) | (Novo Nordisk) |
| Proteinase K (60 mg/ml) | (Roche Diagnostics, Cat. No. 1 964 372) |
| Subtilisin A (19 mg/ml) | (Novo Nordisk) |
| ESPERASE ® (24 mg/ml) (subtilisin from *Bacillus lentus*) | (Novo Nordisk) |
| CHIRAZYM ® (31 mg/ml) | (Roche Diagnostics) |
| NOVOZYME ® 539 | (Novo Nordisk) |
| Novo 47002 | (Novo Nordisk) |
| NOVOCOR ™ PL | (Novo Nordisk) |
| PRONASE ® (proteinase from *Streptomyces Griseus*) | (Roche Diagnostics, Catalog No. 165 921) |

1.2 Buffers 1.2.1 Lysis- and Binding Buffer:

Lysis-and binding buffer has been prepared from:

5 M Guanidiumthiocyanate

15% Polydocanol

1% Dithiothreitol (DTT)

15 mM Bis-TRIS, pH 6.0

1.2.2 Washiini buffer:

Washing buffer had the following composition:

50% Ethanol 50 mM NaCl 10 mM Bis-TRIS, pH 6.0

1.2.3 Elution Buffer:

Elution buffer has been RNase-free destined water.

1.3 Magnetic Glass Particles

Magnetic glass particles as described in WO01/37291 have been suspended in isopropanol at a concentration of 6 mg/ml. The said magnetic glass particles can also be taken from the MagNA Pure LC DNA Isolation Kit I (Roche, Mannheim, Germany).

1.4 Buffers for the Protease Activity Assay

Buffer: 50 mM Tris/HCl pH 8.2

10 mM calcium chloride

Substrate solution: 200 mM Suc-Ala-Ala-Pro-Phe-p-nitroanilide in dimethylsulfoxide (DMSO)

1.4 Preparation of PCR-Grade Esperase

PCR-grade esperase was prepared as follows. All equipment was incubated overnight in 2M NaOH solution.

1.4.1 Dialysis 200 ml of 70 mg/ml esperase dissolved in a suitable buffer (e.g., Esperase HP F solution from Novozyme, Copenhague) was dialyzed over 3 days against 3×12 L 10 mM Tris pH 5.5, 5 mM Calcium acetate, 5 mM calcium chloride, 1 mM EDTA, 50% glycerol. The pH of the buffer was adjusted with acetic acid to 5.5. The dialysate (approximately 70 ml, 150 mg protein per ml) was then diluted with freshly prepared dialysis buffer to a protein concentration of approximately 80 mg/ml.

1.4.2 Ultrafiltration

Approximately. 50 ml freshly prepared dialysis buffer was filtered through 100 kDa Omega (Pall Filtron) membrane. After that the dialysate was filtrated through the membrane. After filtration the membrane was washed with 20 ml dialysis buffer. The filtrate was diluted with the filtrated dialysis buffer to a protein concentration of 60±5 mg/ml.

1.4.3 Sterilization

The filtrate was filtrated through a 0.22 μ membrane (Pall Filtron).

1.4.4 Optional Purification Steps

Esperase solutions that contained nucleases or nuclease activity, were purified by one of the following purification steps to remove the contaminations prior to the above described procedure:

1.4.4.1 Ammonium Sulfate Crystallization 200 ml Esperase solution is diluted with 400 ml 10 mM Tris-HCl, pH 7.5; 5 mM calcium acetate; 5 mM calcium chloride; 1 mM EDTA. 108.6 g ammonium sulfate is added to the solution in small portions and the solution is afterwards stirred for 1 hour at room temperature. The solution is centrifugated. The precipitate is washed twice with 600 ml 10 mM Tris-HCl; 5 mM calcium acetate; 5 mM calcium chloride; 1 mM EDTA; 1.25 M ammonium sulfate pH=7.5. The precipitate is dissolved in 200 ml 10 mM Tris-HCl; 5 mM calcium acetate; 5 mM calcium chloride; 1 mM EDTA pH=7.5.

1.4.4.2 Heparin-Sepharose ff-chromatography 4 ml Heparin-Sepharose ff. (supplier: Amershan Pharmacia) is filled in a column and equilibrated with 10 mM Tris-HCl, pH 7.5; 5 mM Calcium acetate; 5 mM Calcium chloride; 1 mM EDTA. 200 ml Esperase solution is passed through the column with a flow of 2 ml/min. Afterwards the column is washed with 10 ml of the equilibration buffer. All fractions with Esperase are pooled.

EXAMPLE 2

Sample Preparation Method and Polymerase Chain Reaction

2.1 Protease Digestion and Lysis

80 μl protease solution is mixed with 420 μl sample material (e.g. plasma with a specific virus concentration) and mixed. 500 μl lysis- and binding buffer are added and the solution is mixed for 10 minutes at room temperature.

2.2 Binding

500 μl of the suspension of magnetic glass particles in isopropanol are added and the solution is mixed for 20 minutes at room temperature.

2.3 Washing

After the binding step the magnetic glass particles are separated from the solution by a magnet and washed five times with 750 μl washing buffer per wash cycle.

2.4 Elution

After the last wash cycle the magnetic glass particles are separated by a magnet from the suspension and the washing buffer is sucked off from the magnetic glass particles and 100 μl elution buffer are added. The suspension is mixed and incubated for 15 minutes at 80° C. After the elution step the magnetic glass particles are separated again by a magnet and the supernatant containing the viral nucleic acid is harvested.

2.5 Protocol Amplification/Detection

With the exception of the primers all reagents were purchased from Roche Molecular Biochemicals.

| Master Mix HCV: Reagent | conc./PCR |
|---|---|
| Bicine Buffer (pH 8.3) | 1 x |
| MnOAc | 2.5 mM |
| dNTP Mix with dUTP | |
| dUTP | 0.6 mM |
| dATP/dCTP/dGTP | 0.2 mM each |
| Primer KY 80 (F) | 300 nMol |
| Primer KY 78-bio (R) | 300 nMol |
| Tth-Polymerase | 10 U |
| Uracil-N-glycosylase (UNG) | 2 U |
| Bicine Buffer (pH 8.3) | 1 x |
| MnOAc | 1.25 mM |
| dNTP Mix with dUTP | |
| dUTP | 0.6 mM |
| dATP/dCTP/dGTP | 0.2 mM each |
| Primer SK 462-bio (F) | 200 nMol |
| Primer SK 431-bio (R) | 200 nMol |
| Tth-Polymerase | 15 U |
| UNG | 2 U |
| DNA-Master Mix | 1 x |
| $MgCl_2$ | 3.0 mM |
| Primer 1 (F) | 200 nMol |
| Primer 2(bio (R)) | 200 nMol |
| UNG | 2 U |

20 μL of the eluate from the sample preparation process which contains the target nucleic acid, e.g. viral RNA (HCV, HIV) or viral DNA (HBV) are mixed which 100 μl master mix. Amplification is performed on a Perkin-Elmer Thermocycler 9600 with the following thermocycler programms:

| HCV: | | |
|---|---|---|
| UNG step | 1 x | 10 min 37° C. |
| RT step | 1 x | 30 min 60° C. |
| | 1 x | 1 min 95° C. |
| PCR | 2 x | 10 sec 95° C. |
| | | 20 sec 60° C. |
| | 33 x | 15 sec 90° C. |
| | | 20 sec 60° C. |
| | 1 x | 7 min 72° C. |
| HIV: | | |
| UNG step | 1 x | 10 min 37° C. |
| RT step | 1 x | 30 min 60° C. |
| PCR | 4 x | 10 sec 95° C. |
| | | 10 sec 55° C. |
| | | 10 sec 72° C. |
| | 31 x | 10 sec 90° C. |
| | | 10 sec 60° C. |
| | | 10 sec 72° C. |
| HBV: | | |
| UNG step | 1 x | 10 min 37° C. |
| PCR | 35 x | 30 sec 92° C. |
| | | 30 sec 55° C. |
| | | 40 sec 72° C. |

For the detection of the amplified material, a very sensitive nonisotopic approach based on electrochemiluminescence (ECL) was used. Ruthenium-tris(bipyridyl)-labeled oligonucleotides (capture probes) were hybridized specifically to the biotinylated denatured amplicons. Subsequent, this hybrid was bound to the surface of streptavidin-coated magnetic beads. After the beads were captured on an electrode by using a permanent magnet, the ECL reaction of the ruthenium label was triggered by voltage application. For details of the ECL detection process, see Hoyle et al. (13). The totally automated ECL detection was performed on an instrumental platform (preprototype of Elecsys 1010; Boehringer Mannheim GmbH).

| HCV: | |
|---|---|
| KY80: | SEQ ID NO: 4 |
| KY78: | SEQ ID NO: 5 |
| Probe: | SEQ ID NO: 6 |
| HIV: | |
| SK 462: | SEQ ID NO: 7 |
| SK 431: | SEQ ID NO: 8 |
| Probe: | SEQ ID NO: 9 |
| HBV: | |
| Primer 1: | SEQ ID NO: 10 |
| Primer 2: | SEQ ID NO: 11 |
| Probe: | SEQ ID NO: 12 |

Result

| Virus | Proteinase K (ECL counts × $10^{-3}$) | Pronase (ECL counts × $10^{-3}$) | Subtilisin A (ECL counts × $10^{-3}$) | Esperase (ECL counts × $10^{-3}$) | Chirazym (ECL counts × $10^{-3}$) |
|---|---|---|---|---|---|
| HIV | 278 | 62 | 62 | 210 | 214 |
| HCV | 184 | 22 | 49 | 179 | 249 |
| HBV | 371 | 30 | 241 | 300 | 446 |

Only the use of esperase and chirazym for the degradation of plasma proteins in the sample preparation process results in an ECL signal comparable to the signal generated by the use of proteinase K in the sample preparation process.

EXAMPLE 3

Protocol Chromatographic Analysis of Plasma Protein Digestion

Protein digestion and lysis were carried out as described. Each 100 µl of the lysated solution were injected onto an high pressure liquid chromatography instrument (HPLC) (Dionex, Gynkothek) and separated on an reversed phase column (C4, Vydac, 4.6 mm×150 mm) in a linear gradient of 0–80% acetonitrile in 0.1% trifluoroacetic acid (TFA). Peaks were detected at a wavelength of 220 nm and 280 nm.

| | Plasma Protein Digestion | |
|---|---|---|
| Protease | With unstressed Protease | with Protease stressed by thermal treatment (after 3 day incubation at 45° C. in storage buffer* |
| Esperase | ++ | ++ |
| Proteinase K | ++ | ++ |
| Pronase | ++ | − |
| Subtilisin A | ++/+ | + |
| Alcalase | + | not tested |
| Novozyme 539 | + | not tested |
| Novo 47002 | − | not tested |
| Novocor PL | − | not tested |

*Storage buffer composition: 10 mM Tris acetate, 5 mM calcium chloride, 5 mM calcium acetate, 1 mM EDTA, 50% (V/V) glycerin with a pH value of 5.5

Figure 1B:
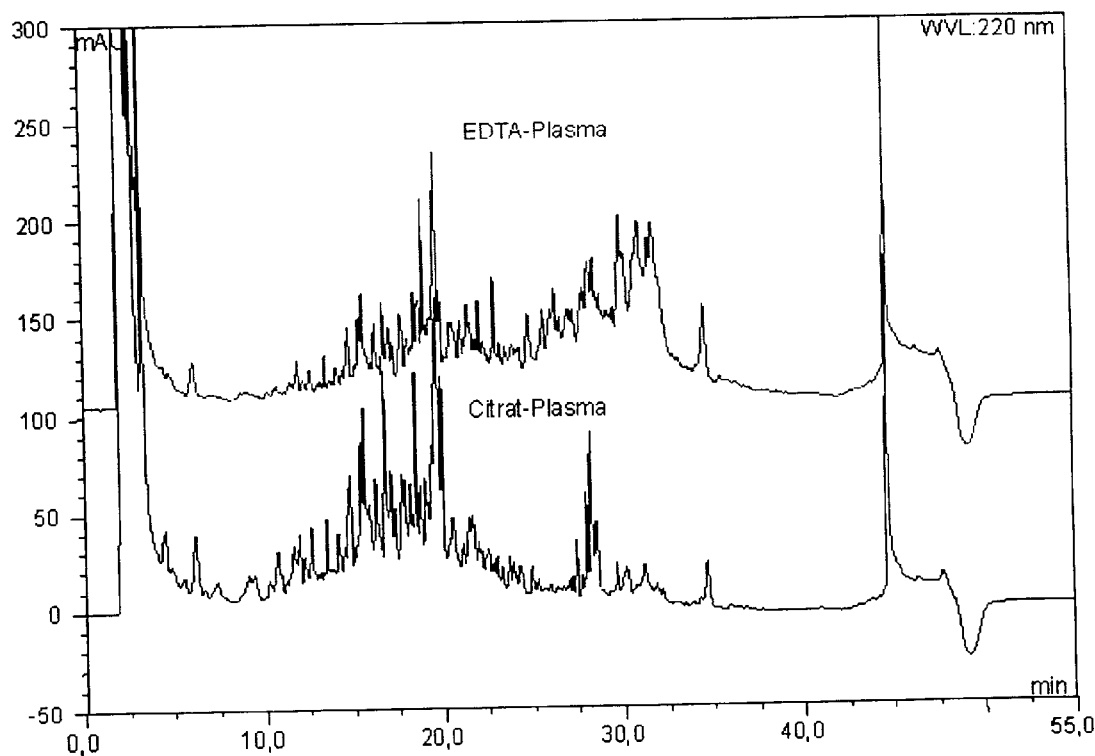
FIG. 1b: Comparison of the digestion of EDTA plasma versus citrate plasma with proteinase K as analyzed by high pressure liquid chromatography

In FIG. 1, the comparison of the digestion of EDTA plasma versus citrate plasma with Esperase (see FIG. 1a) and proteinase K (see FIG. 1b) is shown.

EXAMPLE 4

Evaluation of the pH Optimum

Figure 2:
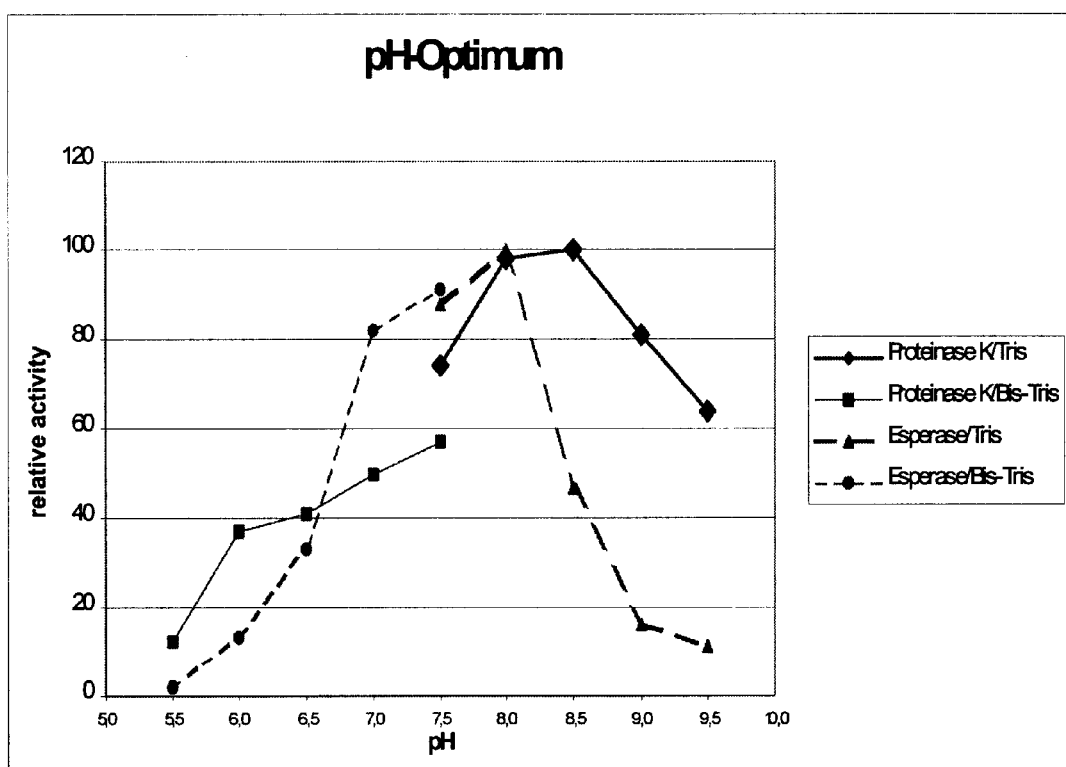
FIG. 2: Determination of the pH Optimum of Esperase

The pH optimum of esperase was compared to the pH optimum of proteinase K using the buffers as basically described under 1.1.4 with a varying pH. The pH optimum was more in the neutral pH region as compared to proteinase K (see FIG. 2). Sample: 10 mg protein are dissolved in 1 ml distilled water. Before the determination, the sample is diluted with dest. water so that the increase in the extinction in the test is between 0.02 and 0.05 E.

Sample buffer:
pH-range: 5.5 bis 7.5: 50 mM Bis-Tris+10 mM $CaCl_2$ are adjusted with 2 N HCl or 2 N NaOH to the respective pH.
pH-range 7.5 bis 9.5: 50 mM Tris-Base+10 mM $CaCl_2$ are adjusted with 2 N HCl or 2 N NaOH to the respective pH.
Substrate: Suc-Ala-Ala-Pro-Phe-p-nitroanilide (200 mM dissolved in Dimethyl sulfoxide (DMSO)).
Measurement:
Pipetting scheme: 2.00 ml sample buffer
0.02 ml substrate
0.05 ml sample
Temperature for measurement: 25° C.
Wavelength for measurement: 405 nm
Evaluation: The linear increase in extinction (de/min) is determined between 2 and 6 min.
Layer thickness: 1 cm $$\text{Activity} = \frac{2.07 * dE/min}{10.4(\varepsilon) * 0.05 * 1} * \text{dilution (U/ml)}$$

Relative Activity: For each sample, the highest measured activity is regarded as the value of 100% and the activities at other pH-values are evaluated by determining the percental relation to this value.

EXAMPLE 5

Evaluation of the Enzymatic Activity in the Presence of Chaotropic Agents

Figure 3:
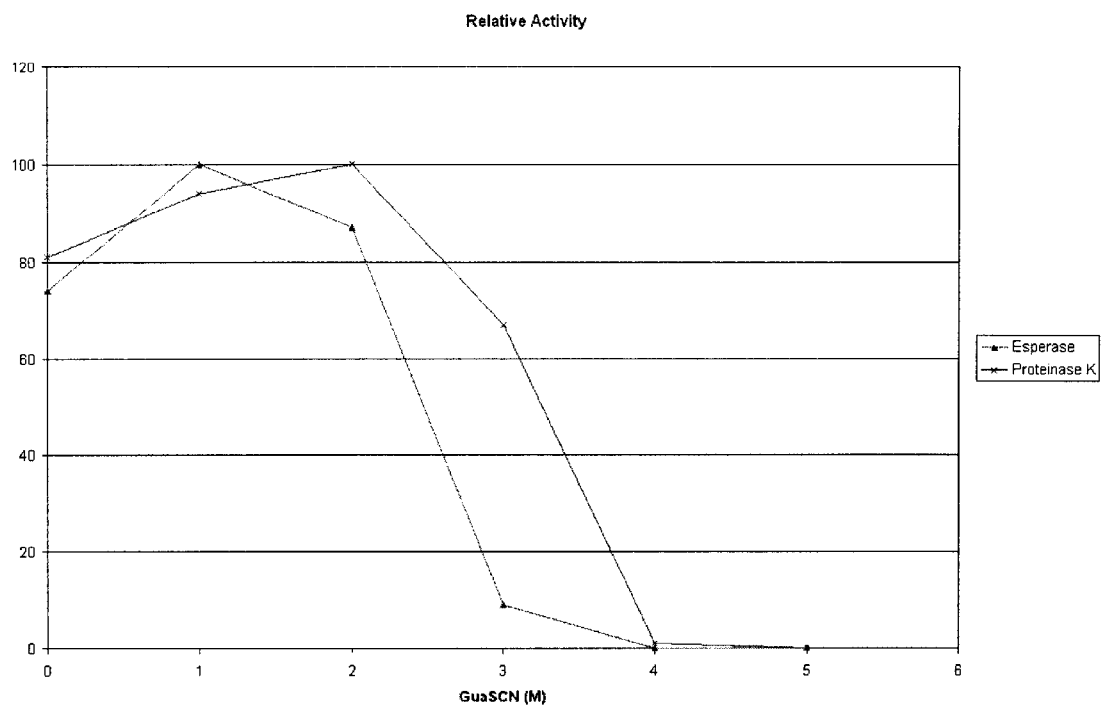
FIG. 3: Determination of the residual activity of Esperase versus proteinase K in dependence of the concentration of a chaotropic agent. The highest activity is set to a value of 100% and the other concentrations are calculated relative to the highest value.
Figure 4:
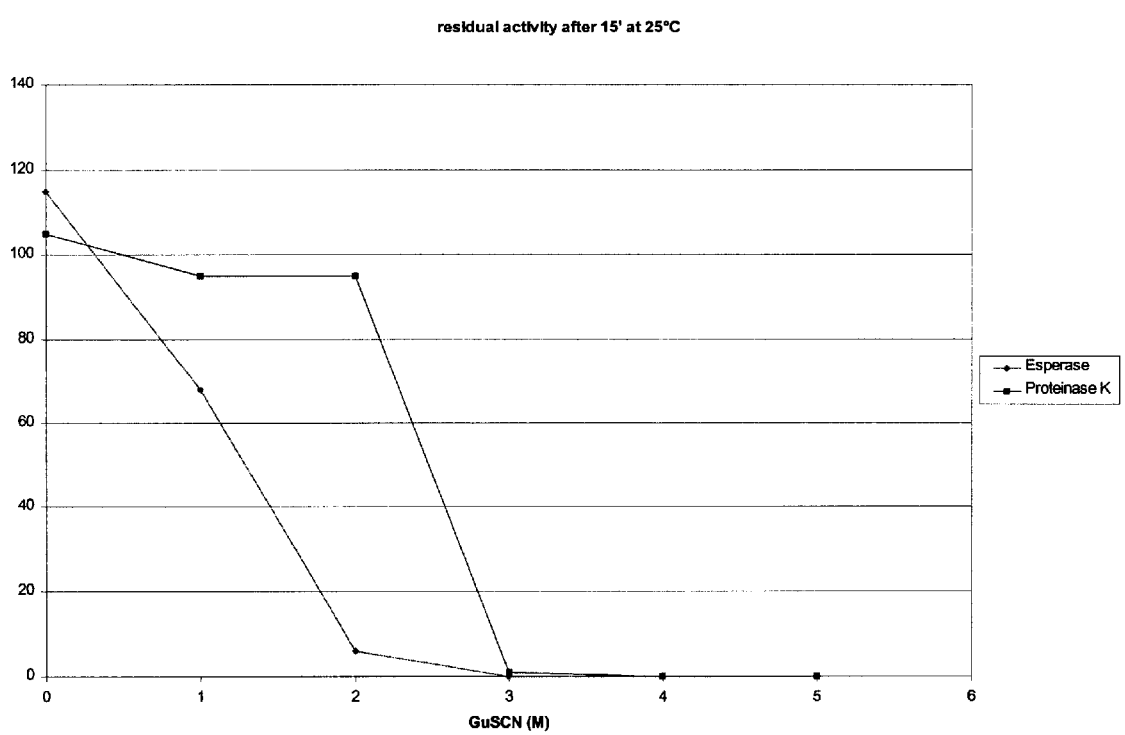
FIG. 4: Determination of the stability of Esperase versus proteinase K in dependence from the concentration of guanidinium thiocyanate. The activity of the protease is measured directly after the addition of guanidinium thiocyanate and after 15 min at 25° C. in the presence of guanidinium thiocyanate. The percentage of the residual activity at different guanidinium thiocyanate concentrations is shown in this figure.

The enzymatic activity of esperase was compared to the enzymatic activity of proteinase K in the presence of chaotropic agents using the buffers as basically described under 1.1.4 with increasing amounts of chaotropic agent. Esperase retained more activity in the presence of chaotropic agents (see FIG. 3 and FIG. 4). This lower residual activity is advantageous as the protein digestion by esperase is very quick in the presence of chaotropic agent (≦1 min) and as esperase has a low residual activity. This is of advantage as less active esperase is transferred into the amplification reaction where it may disturb the amplification reaction.

Protease solution: 20 mg/ml Protease
Sample: 500 µl chaotropic agent
50 µl protease solution.
The activity of the protease is determined in various solutions. Then, the sample is incubated for 15 min at 25° C. and the residual activity determined in various agents.
Determination of the activity:
Test buffer: 50 mM Tris.HCl pH=8.2; 10 mM $CaCl_2$
Substrate: 200 mM Suc-Ala-Ala-Prp-Phe-p-nitroanilide in DMSO
Measuring temperature: 25° C.
Measuring wavelength: 405 nm
Evaluation: see evaluation of the pH Optimum.

EXAMPLE 6

Storage Stability

Figure 5:
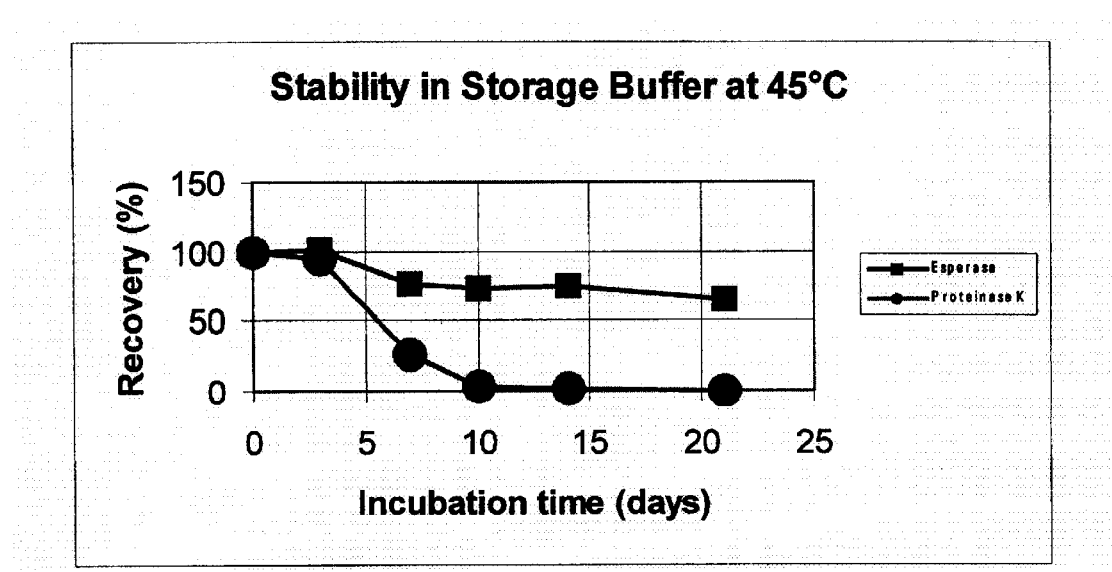
FIG. 5: Stability in Storage Buffer (composition: 10 mM Tris acetate, 5 mM calcium chloride, 5 mM calcium acetate, 1 mM EDTA, 50% (V/V) Glycerin with a pH value of 5.5) of esperase versus proteinase K.

The stability of the proteases was determined by following the proteolytic activity under thermal stress in storage buffer (composition: 10 mM Tris acetate, 5 mM calcium chloride, 5 mM calcium acetate, 1 mM EDTA, 50% (V/V) Glycerin with a pH value of 5.5). A kinetic assay with Suc-Ala-Ala-Pro-Phe-p-nitroanilide as a substrate was used. Shortly before use the protease sample has to be diluted to a concentration of 1–3 µg/ml with distilled water. 2 ml buffer were mixed with 0.02 ml substrate and 0.05 ml diluted sample. The release of p-nitroaniline from the substrate at 25° C. was measured photometrically at 405 nm. The time-curve of the stability of Esperase in comparison to proteinase K is shown in FIG. 5. The result of this experiment is that it could be shown that Esperase is very stable in storage buffer even after a prolonged period of time.

| Protease | Remaining activity after 3 day incubation at 45° C. in storage buffer (composition see above) |
|---|---|
| Esperase | 88% |
| Proteinase K | 94% |
| Pronase | 89% |
| Subtilisin A | 45% |

LIST OF REFERENCES

"Bioanalytik", Lottspeich and Zorbas (eds.), 1$^{st}$ edition 1998, Spektrum Akademischer Verlag, Heidelberg, Berlin, Germany
Abramson and Myers, 1993, Current Opinion in Biotechnology 4:41–47
Anal. Biochem. 121, 382–387 (1982)
Anal. Biochem. 175, 196–201 (1988)
Anal. Biochem. 201, 166–169 (1992)
Ausubel et al.: Current Protocols in Molecular Biology 1987, J. Wiley and Sons, NY, USA
Barany, 1991, PCR Methods and Applic. 1:5–16
Barany, 1991, Proc. Natl. Acad. Sci. USA 88:189–193
DE 3724442
EP 110165
EP 396 608
EP 439 182
GB 91/00212
Guatelli et al., 1990, Proc. Natl. Acad. Sci. USA 87:1874–1878
Hoyle, N. R., B. Eckert, and S. Kraiss. 1996
Jacobs et al., 1985, Nucl. Acids Res. 13: 8913–8926
Jany and Mayer, 1985, Biol. Chem. Hoppe-Seyler 366: 485–492
Jany and Mayer, 1985, Biol. Chem. Hoppe-Seyler 366: 584–492
Kraut, 1977, Ann. Rev. Biochem. 46: 331–358
Kurihara et al., 1972, J. Biol. Chem. 247: 5629–5631
Kwoh et al., 1989, Proc. Natl. Acad. Sci. USA 86:1173–1177
Meloun et al., 1985, FEBS Lett. 183: 195–200
Nedkov et al., 1985, Biol. Chem. Hoppe-Seyler 366: 421–430
Priest, 1977, Bacteriological Rev. 41: 711–753
Proc. Natl. Acad. USA 76, 615–691 (1979)
Sambrook et al.: Molecular Cloning, A Laboratory Manual, 2nd Addition, Cold Spring Harbour Laboratory Press, Cold Spring Harbour, N.Y., USA
Stahl and Ferrari, 1984, J. Bacteriol. 158: 411–418
Svendsen et al., 1986, FEBS Lett. 196: 228–232
U.S. Pat. No. 3,723,250
U.S. Pat. No. 4,683,195
U.S. Pat. No. 5,130,238
U.S. Pat. No. 5,210,015
U.S. Pat. No. 5,386,024
U.S. Pat. No. 5,487,972
U.S. Pat. No. 5,741,694
U.S. Pat. No. 5,804,375
Vasantha et al., 1984, J. Bacteriol. 159: 811–819
Wallace, 1989, Genomics 4:560–569
Walsh, 1979, Enzymatic Reaction Mechanisms. W. H. Freeman and Company, SanFrancisco, Chapter 3
Whelen and Persing (1996). Annu. Rev. Microbiol. 50, 349–373
White, Handler, and Smith, 1973 "Principles of Biochemistry," Fifth Edition, McGraw-Hill Book Company, N.Y., pp. 271–272
WO 89/06279
WO 90/01069
WO 92/02638
WO 92/0880A
WO 98/04730
WO 98/20115

The disclosures of these and other cited publications and patents are incorporated herein by reference.

What is claimed is:

1. A method for the analysis of a target non-proteinaceous component of a mixture of non-proteinaceous and proteinaceous components derived from a biological sample comprising the steps of
   a) incubating the mixture with a protease comprising an amino acid sequence which is at least 80% identical to SEQ ID NO: 1; and
   b) analyzing the target non-proteinaceous component.

2. The method according to claim 1 wherein the amino acid sequence of the protease is identical to SEQ ID NO: 1.

3. The method according to claim 1 wherein the amino acid sequence of protease comprises SEQ ID NO:1, a proteolytic derivative thereof having protease activity or SEQ ID NO:2.

4. The method according to claim 1 wherein the amino acid sequence of the protease is encoded by a nucleic acid comprising the nucleic acid sequence SEQ ID NO:3 or a part thereof or a degenerate version of either.

5. A method according to claim 1 wherein the biological sample is a fluid from the human or animal body.

6. The method according to claim 1 wherein the biological sample is blood, blood plasma, blood serum or urine.

7. The method according to claim 1 wherein the biological sample comprises bacterial cells, eukaryotic cells, viruses or mixtures thereof.

8. The method according to claim 1, wherein after the incubation step the target non-proteinaceous component is bound to a material with an affinity thereto, optionally washed and optionally released from the material with an affinity thereto.

9. The method according to claim 1 wherein the non-proteinaceous component comprises a nucleic acid.

10. The method according to claim 9 wherein the nucleic acid comprises DNA or RNA or both.

11. A method for the analysis of a target nucleic acid component of a mixture comprising the target nucleic acid component, and a proteinaceous component whereby the mixture is derived from a biological sample, which method comprises the steps of
   a) incubating the mixture with a protease comprising an amino acid sequence which is at least 80% identical to the amino acid sequence of SEQ ID NO: 1,
   b) optionally amplifying the target nucleic acid component, and
   c) determining or detecting the target nucleic acid component, wherein the target nucleic acid component is analyzed.

12. The method according to claim 11 wherein the amino acid sequence of the protease is identical to SEQ ID NO: 1.

13. The method according to claim 11 wherein the amino acid sequence of the protease comprises SEQ ID NO:1, a proteolytic derivative thereof having protease activity or SEQ ID NO:2.

14. The method according to claim 11 wherein the amino acid sequence of the protease is encoded by a nucleic acid comprising the nucleic acid sequence SEQ ID NO:3 or a part thereof or a degenerate version of either.

15. The method according to claim 11 wherein the biological sample is a fluid from a human or animal body.

16. The method according to claim 11 wherein the biological sample is blood, blood plasma, blood serum or urine.

17. The method according to claim 11 wherein the target nucleic acid component comprises DNA or RNA or both.

18. The method according to claim 17 wherein the DNA or RNA or both is derived from a virus or a microorganism.

19. The method according to claim 18 wherein the virus is hepatitis B virus, hepatitis C virus or human immunodeficiency virus.

20. The method according to claim 11 wherein the target nucleic acid component is amplified with the polymerase chain reaction.

21. The method according to claim 11 wherein after step a) the target nucleic acid component is bound to a material with an affinity to nucleic acids, optionally washed and optionally released from the material.

22. The method according to claim 21 wherein the material with an affinity to nucleic acids comprises a material with a silica surface.

23. The method according to claim 22 wherein the material with a silica surface is a glass.

24. The method according to claim 21 wherein the material with an affinity to nucleic acids is a composition comprising magnetic glass particles.

25. The method according to any of the claims 1 to 24, wherein the analysis is a diagnosis of a disease or a pathogen.

26. A kit comprising a protease comprising an amino acid sequence, which is at least 80% identical to SEQ ID NO:1, and a material with an affinity to nucleic acids, wherein the material with an affinity to nucleic acids comprises a material with a silica surface.

27. The kit according to claim 26 wherein the material with a silica surface is a glass.

28. A kit comprising a protease comprising an amino acid sequence, which is at least 80% identical to SEQ ID NO:1, and a material with an affinity to nucleic acids, wherein the material with an affinity to nucleic acids is a composition comprising magnetic glass particles.

29. The kit according to claim 27 wherein the kit additionally comprises a lysis buffer, a washing buffer and an elution buffer.

30. A composition comprising a protease comprising an amino acid sequence which is at least 80% identical to SEQ ID NO: 1, in a solution 10 mM Tris acetate pH 5.5, 5 mM calcium acetate, 1 mM EDTA, and 50% (V/V) Glycerin.

31. The composition according to claim 30 wherein the amino acid sequence of the protease is identical to SEQ ID NO: 1.

32. The composition according to claim 30 wherein the amino acid sequence of the protease comprises SEQ ID NO:1, a proteolytic derivative thereof having protease activity or SEQ ID NO:2.

33. The composition according to claim 30 wherein the amino acid sequence of the protease is encoded by a nucleic acid comprising the nucleic acid sequence SEQ ID NO:3 or a part thereof or a degenerate version of either.

* * * * *